United States Patent [19]

Harrison et al.

[11] Patent Number: 5,373,852
[45] Date of Patent: Dec. 20, 1994

[54] MONITORING UTERINE CONTRACTIONS BY RADIOTELEMETRIC TRANSMISSION

[75] Inventors: Michael R. Harrison, San Francisco; Russell W. Jennings, Pacifica, both of Calif.

[73] Assignee: The Regents of the University of California, Oakland, Calif.

[21] Appl. No.: 81,133

[22] Filed: Jun. 25, 1993

[51] Int. Cl.⁵ .................................... A61B 5/0488
[52] U.S. Cl. ................................ 128/733; 128/736; 128/775; 128/778; 128/903
[58] Field of Search ............... 128/733, 736, 738, 775, 128/778, 903

[56] References Cited

U.S. PATENT DOCUMENTS

| Re. 31,158 | 2/1983 | Carter et al. | 128/778 X |
|---|---|---|---|
| 4,256,118 | 3/1981 | Nagel. | |
| 4,408,615 | 10/1983 | Grossman. | |
| 4,513,295 | 4/1985 | Jones et al. | |
| 4,738,268 | 4/1988 | Kipnis | 128/778 X |
| 4,944,307 | 7/1990 | Hon et al. | 128/778 X |

(List continued on next page.)

FOREIGN PATENT DOCUMENTS 2826391 of 0000 Germany.

OTHER PUBLICATIONS

Siggar, J. N.; Harding, R.; Jenkin, G. "Relationship Between Electrical Activity of the Uterus and Surgically Isolated Myometrium in the Pregnant and Non–Pregnant Ewe", *J. Reprod. Fert.*, vol. 70, pp. 103–114, 1984.

Neuman, M. R. "Applications of Biotelemetry in Perinatal Medicine", *Biotelemetry VIII*, pp. 121–128, 1984.

Seitchik, J.; Hayashi, R. H. "Intrauterine Pressure Waveform Characteristics: Potential Use for Monitoring Uterine Contractility in Labor", *Uterine Physiology, Proc. of a Brooklodge Workshop*, Ed. Friedman, B612.6, Ut2.

Guha, S. K. "Uterine Contraction Monitoring", *Bioengineering in Reproductive Medicine*, CRC Press, 207–210.

Smith, R. P. "A Brief History of Intrauterine Pressure Measurement", *Acta Obstet Gynecol Scand Suppl.*, vol. 129, pp. 5–24.

Svenningsen, L.; Jensen, O. "Application of Fiberoptics to the Clinical Measurement of Intrauterine Pressure in Labor", *Acta Obstet Gynecol Scand*, vol. 65, pp. 551–555, 1986.

Philips, G. F.; Calder, A. A. "Units for the Evaluation of Uterine Contractility", *British Journal of Obstetrics and Gynecology*, vol. 94, pp. 236–241, Mar. 1987.

Hon, E. H.; Paul, R. H. "Quantitation of Uterine Activity", *Obstetrics and Gynecology*, vol. 42, No. 3, pp. 368–370, Sep. 1973.

Steer, P. J.; Carter, M. C. "Electronic Assessment of Uterine Activity", Chapter 11 of an unidentified periodical (undated), pp. 136–146.

Cross, D. T.; Threlfall, W. R.; Rogers; R. C.; Kline, R. C. "Uterine Electromyographic Activity in Horse (List continued on next page.)

*Primary Examiner*—Angela D. Sykes
*Attorney, Agent, or Firm*—Fisher & Associates

[57] ABSTRACT

A uterine monitor is provided for gathering characteristic data such as maternal uterine electromyogram, uterine temperature and intra-uterine pressure so that the onset of parturition or labor may be determined. The uterine monitor comprises a remote sensing unit, the remote sensing unit containing sensors which sense uterine temperature, intra-uterine pressure and uterine electromyogram. A transceiver is housed in the remote sensing unit and outputs the sensed signals to an external antenna. A monitoring station is provided for monitoring the sampled signals. Additionally a medication dispenser is provided which may be actuated by the monitoring station upon the onset of parturition or labor.

39 Claims, 8 Drawing Sheets

U.S. PATENT DOCUMENTS

| | | |
|---|---|---|
| 4,967,761 | 11/1990 | Nathanielsz ............... 128/733 |
| 5,038,800 | 8/1991 | Oba . |
| 5,042,503 | 8/1991 | Torok et al. ............... 128/778 X |
| 5,085,224 | 2/1992 | Galen et al. . |
| 5,184,619 | 2/1993 | Austin . |
| 5,212,476 | 5/1993 | Maloney ............... 128/733 X |

OTHER PUBLICATIONS

Mares as Measured by Radiotelemetry", *Theriogenology*, vol. 26, No. 5, Nov. 1991.

Cross, D. T.; Threlfall, W. R. Kline, R. C. "Telemetric Monitoring of Body Temperature in the Horse Mare", *Theriogenology*, vol. 36, No. 5, Nov. 1991.

Cross, D. T.; Threlfall, W. R.; Kline, R. C. "Body Temperature Fluctuations in the Periparturient Horse Mare", Theriogenology, vol. 37, pp. 1041–1048, 1992.

Haluska, G. J.; Lowe, J. E.; Currie, W. B. "Electromyographic Properties of the Myometrium Correlated with the Endocrinology of the Pre-Partum and Post-Partum Periods and Parturition in Pony Mares", *J. Reprod. Fert.*, Suppl., vol. 35, pp. 553–564, 1987.

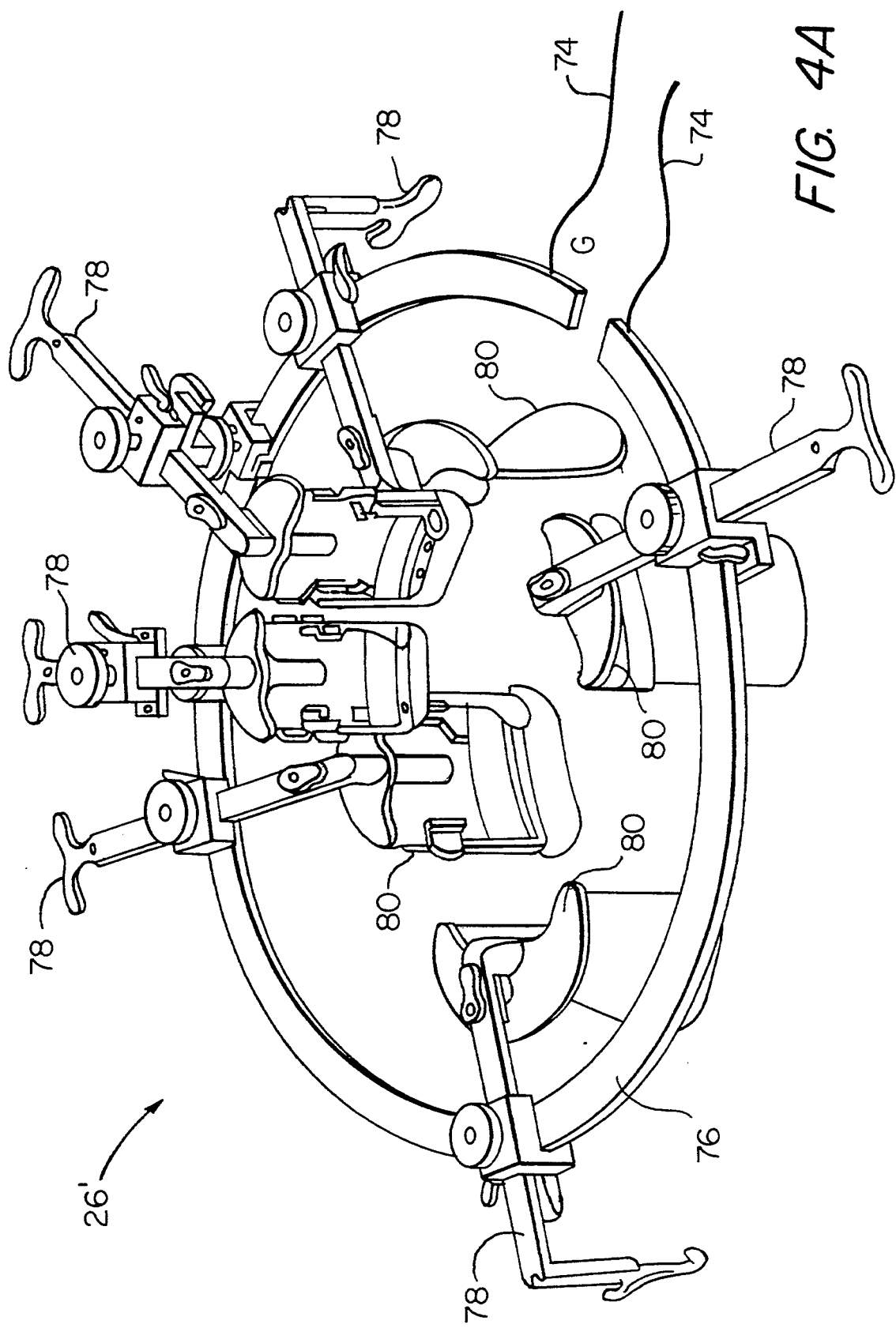

MATERNAL ELECTROCARDIOGRAM

FETAL ELECTROCARDIOGRAM

MONITORING UTERINE CONTRACTIONS BY RADIOTELEMETRIC TRANSMISSION

CROSS-REFERENCE TO RELATED APPLICATIONS

This application makes reference to the following co-pending U.S. Applications. The first application is U.S. application Ser. No. 08/081,139, entitled "Monitoring Fetal Electrocardiogram by Radiotelemetric Transmission", filed Jun. 25, 1993. This application is hereby incorporated by reference.

BACKGROUND OF THE INVENTION

1. Field of the Invention

The present invention relates generally to measuring devices, and more particularly to a measuring device which measures uterine characteristics and automatically responds to conditions indicative of parturition or labor so that appropriate actions may be taken to suppress or manage labor, either by administration of tocolytic agents or other means.

2. Description of the Prior Art

The inability to detect the onset of premature labor or parturition has proved to be a dilemma to both pregnant women and their health care professionals. It is not uncommon for women to unexpectedly give birth before arriving at a medical facility. Additionally, the occurrence of false labor, and the inconveniences related thereto, are commonplace. Thus, there has been an attempt to develop accurate labor detection devices.

Each year in the U.S., 5% of all infants are born prematurely at an enormous cost to the health care system. Premature births account for 85% of neonatal deaths. About 10% of pregnant women in the U.S. are at risk of premature labor. Accurate detection or prediction of the occurrence of premature labor would allow the patient to be appropriately treated to suppress labor, thereby improving the chances that delivery will occur closer to term. The closer the delivery is to term, the lower the mortality rate and the lower the cost post-delivery neonatal care.

Several methods have been employed or proposed for detection or prediction of premature labor. These include both natural and instrument-based means.

Symptomatic self-monitoring is a natural means whereby the mother is educated in the symptoms of uterine contractions or cervical dilatation and receives regular counseling from a nurse. This approach has the advantage that it is non-invasive and inexpensive, since it can be done at home. However, it requires significant discipline, is time consuming for the patient, and lacks uniform accuracy. Mammary stimulation, cervical distensibility, and fetal breathing movements encompass other natural means. However, these methods require that the patient visit a care provider. They are therefore expensive and inconvenient.

Intrauterine pressure (IUP) measurement devices are considered to be the most accurate means available for measuring frequency of occurrence, duration, and intensity of uterine contractions. This technique has frequently been used to validate the accuracy of other methods of monitoring uterine activity. In this method a transvaginal catheter is inserted into the uterus. Open lumen fluid-filled catheters may be used, but require regular flushing to keep the lumen free of cellular debris. Catheters have been constructed with a balloon tip to eliminate the need for regular flushing. Microbal-loon-tipped catheters provide poor accuracy Larger balloons provide better accuracy but their presence leads to irritation and artifactual stimulation to both uterus and fetus. In addition, their use is restricted to bed-ridden patients and there is a risk infection. Catheters that employ a solid state pressure transducer at the tip or fiber optic technology have also been used. These devices are available from companies such as Hewlett Packard (HP Model 113975A). These devices are useful only in a limited number of circumstances and only for bed-ridden patients, typically following a membrane rupture. Additionally, these devices increase the risk of infection. An implantable pressure telemetry device has also been used (Smyth, 1960) for monitoring intrauterine pressure. This device has been introduced into the uterine cavity external to the membranes to measure IUP following induction of labor. The authors suggest its use to "extending obstetric research and treatment control." No reference is made to using this device as a tool for prediction or detection of premature labor.

With the exception of symptomatic self-monitoring, use of the above methods has been restricted to a care provider's office. However, successful treatment preterm labor depends on early diagnosis (Iam, et. al., 1990) and these methods do not provide the timely information needed to effect prompt intervention and arrest labor. Methods suitable for monitoring patients as they go about their daily activities present a significant advantage in early diagnosis of preterm labor.

The guard-ring tocodynamometer provides a non-invasive means for monitoring uterine activity and represents the current state-of-the-art for detecting premature labor in ambulatory patients. This device is placed on the maternal abdomen and held in place by an elastic belt. It employs a "guard-ring" to flatten the abdomen within an area over which pressure applied to a sensing diaphragm by the abdominal tissues is sensed. Pressure measurements taken at this flattened area are representative of intrauterine pressures. Some commercially available tocodynamometers are capable of transmitting data to a clinic or doctors office via telephone lines. These devices are manufactured by Tokos of Santa Ana, Calif.; Healthdyne of Marietta, Ga.; and Orion. of Ft. Meyers, Fla. All of these devices are ineffective under certain circumstances. Additionally, they are prone to false alerts since a rise in abdominal pressure may be caused by application of external forces such as exercise, a hand pushing on the abdomen, or gastric activity.

Parturition may be determined by utilizing information from physiological changes, such as temperature changes, vulva swelling, cervical dilation, and uterine contractions with varying degrees of success and forewarning.

Several technologies, such as ultrasound and remote sensing, have been utilized in the determination of the onset of parturition. For example, U.S. Pat. No. 3,606,879 (Estes) discloses an ultrasonic apparatus which is used for monitoring uterine contractions and cervical dilations by measuring the change in transit times of each pulse of ultrasonic energy. Additionally, fetal heartbeat may be determined by monitoring the change in frequency, due to a doppler effect, of an ultrasonic wave which passes through a fetus.

In an attempt to detect parturition, temperature sensors have been utilized to detect temperature changes in animals. For example, U.S. Pat. No. 4,651,137 (Zartman) discloses an intravaginal parturition alarm and method for its use. The device comprises an anchor, a temperature sensing means affixed to the anchor, and an alarm means. The anchor has a diameter that is smaller than an interior diameter of a posterior portion of the animal's vagina at the onset of parturition, but greater than the interior diameter prior to the onset parturition. The anchor's diameter is also smaller than an interior diameter of an anterior portion of the female's vagina before and at the onset of parturition such that the anchor is retained in the anterior portion for a period prior to parturition and expulsed at the onset of parturition. The sensing means senses temperature differential at the location of the anchor before and after expulsion and activates an alarm means based upon this temperature change. Additionally, intravaginal pressure may be measured for a period days prior to parturition by inserting the device and taking a measurement. This process is repeated daily to determine a standard intravaginal temperature for the female at a particular time. As is obvious, this method is highly invidious and will not apply with respect to human females.

Aside from the use of the temperature change upon expulsion of an object from the reproductive tract as an indicator of parturition, others have attempted without success to show a reliable relationship between temperature phenomena and the onset of parturition and related events. Research reports may be summarized as describing a body temperature increase during the latter part of pregnancy, with a substantial drop during the last few days to a few hours before parturition. However, for a number of reasons, the efforts of workers in the field to develop a reliable relationship between temperature phenomena and the onset of parturition have failed.

In fact the prior art would actually lead one away from the use of temperature measurements as a reliable tool in the forecasting and identification of occurrences related to parturition. Researchers in the field generally reported failures in their attempts to use such measurements in forecasting and determining occurrences related to parturition, thus dissuading other researchers from further study. Additionally, with only one exception, no current textbooks on reproductive physiology have been found that comment on any temperature phenomenon related to parturition.

Detection of parturition in animals has been accomplished in various ways. For example, U.S. Pat. No. 4,707,685 (Carrier et al.) discloses a system for detection of parturition which in effect is a continuity circuit. When a cow enters parturition, a thin wire, disposed about the animal's vulva, is broken and thus continuity in an electric circuit is interfered This lack of continuity sets off an alarm. U.S. Pat. No. 4,936,316 (Jewett) discloses the monitoring of the swelling of the animal's vulva.

Body pressure sensors have been utilized in conjunction with gathering information during parturition For example, U.S. Pat. No. 3,989,034 (Hojaiban) discloses an apparatus for determining the heart rate of a fetus during labor. The device comprises a means for receiving a measured fetal heart rate signal; a means for receiving a uterus pressure signal; and a means for determining an actual fetal heart rate based upon the uterine pressure and the measured fetal heart rate.

As may be seen, there are apparatus for detection of the onset of parturition, but these devices have various drawbacks. The accuracy in determining the duration of contractions in the above described devices is very limited, and thus the warning time available to medical professionals is limited to a short period before the onset of parturition.

Other types of sensors include blood flow monitors and heart contraction monitors. U.S. Pat. No. 4,915,113 (Holman) discloses a blood flow monitor comprising a plurality of transducers, an enclosure device, and an external monitor which is coupled to the enclosure by radio-telemetry. U.S. Pat. No. 4,993,427 (Barr et al.) discloses a heart contraction monitor comprising two ultrasonic transducers which are attached to an external monitor by a transmission line.

Other non-instrument based techniques for assessment of labor include symptomatic self monitoring, mammary stimulation, cervical distensibility indexing, and monitoring of fetal breathing movements. Each of these techniques has its advantages and drawbacks. But none of these techniques provides an accurate picture of the onset of parturition or of pre-term labor.

Another major concern in the birthing process is to determine the occurrence of fetal stress syndrome, which may occur before or during parturition. When fetal stress syndrome occurs, the fetus' temperature begins to climb dramatically, and the mother's temperature similarly undergoes a marked temperature increase. In order to reduce the risk of fetal mortality or injury, it is important to administer suitable treatment to remedy the problem as soon as possible. While the prior art has appreciated the importance of suitably administering treatment to the mother and fetus upon the occurrence of fetal stress syndrome, as seen in Weisz, "The Temperature Phenomenon Before Parturition and Its Clinical Importance," J.A.V.M.A. 102:123 (1943), the prior art has failed to adequately provide a means for detecting the onset of fetal stress syndrome and automatically administering the required treatment.

The automatic administration of drugs based upon medical characteristics of the patent are utilized in areas such as high blood pressure treatment, blood oxygen concentration problems, and the treatment of diabetes. For example, U.S. Pat. No. 4,003,379 (Ellinwood) discloses a medication dispenser which is inserted into the body and will dispense upon particular conditions being present. The dispenser comprises at least one sensor, control circuitry, a power source, a dispensing means, and medication storage means. Sensors and logic control circuitry are provided within the dispenser for measuring the existence or absence of a particular condition such as high blood pressure.

U.S. Pat. No. 4,543,955 (Schroeppel) discloses a medical implant which includes a sensor assembly disposed remotely from the implant, signal converting circuitry for converting the signals from the sensor to a coded signal, a transmitting means for transmitting the coded signal, and an activation device for receiving the coded signal and actuating the activation device based upon the coded signal. The parameters sensed by this system are body temperature, blood oxygen concentrations or blood potassium concentrations. Additionally, the activation device may be a drug infusion device.

U.S. Pat. No. 4,596,575 (Rosenberg et al.) discloses an insulin dispenser. The device comprises an implant having a transducer, an electronic control unit, a piezoelectric pump and an insulin reservoir. In operation, an external controller provides an actuation signal to the transducer which in turn sends an actuation signal to the electronic control unit. The control unit actuates the piezoelectric pump which in turn forces insulin to be dispensed from the reservoir.

Although current technology is available for comparing measurements expressed in quantitative form with quantitative tolerance limits and automatically delivering a dose of medication when those limits are exceeded, the evaluation of uterine contractions and the administration of labor inducing or retarding drugs has until now often been a qualitative one beyond the capabilities of the known state of the art identified above.

SUMMARY OF THE INVENTION

It is therefore an object of the present invention to provide a uterine monitoring system which will provide accurate information on maternal health during intra-operative and postoperative periods as well as the onset of labor.

It is a further object to provide a maternal monitor which is implantable.

It is yet another object to provide a uterine monitor which eliminates the possibility of electrical shock and short circuits.

It is yet another object to provide a method for implanting the electrical leads of the uterine monitor to accomplish the goal of eliminating short circuits.

It is yet another object to provide a means for the accurate detection of uterine temperature and electromyogram as well as intra-uterine pressure.

It is yet another object to provide a means for the accurate detection of fetal temperature and electromyogram as well as maternal intrauterine pressure, electromyogram and temperature.

It is yet another object to provide a uterine monitor which may be used to collect data over conventional communication lines.

In all of the above embodiments, it is an object to provide an antenna which provides continuous monitoring of the mother and fetus during intra-operative and postoperative periods as well as during the onset of parturition.

Finally, it is an object of the invention to provide a uterine monitor which may automatically dispense medication upon the existence of particular medical conditions.

According to one broad aspect of the present invention, there is provided a uterine monitor comprising a means for sensing the electromyogram of the mother's uterus and for outputting a electromyogram signal; a means for sensing the intra-uterine pressure of the mother and for outputting a pressure signal; and a means for receiving the electromyogram and pressure signals and for determining the onset of premature or parturition based upon the electromyogram and pressure signals.

According to another broad aspect of the invention, there is provided a uterine monitor further comprising a fetal monitor. The fetal monitor comprises a means for continually sampling the temperature of a fetus and for outputting a sampled fetal temperature signal; a means for continually sampling the electromyogram of a fetus and for outputting a sampled fetal electromyogram signal; and a means for receiving said fetal temperature and electromyogram signals and for determining the existence of fetal conditions based upon the sampled maternal temperature, maternal uterine electromyogram, fetal temperature, and fetal electromyogram. Additionally, a means for continually sampling intra-uterine pressure and for outputting a sampled intra-uterine pressure signal may be provided. This intra-uterine pressure signal in combination with the above signals is utilized to determine the onset and progress of parturition.

Other objects and features of the present invention will be apparent from the following detailed description of the preferred embodiment.

BRIEF DESCRIPTION OF THE DRAWINGS

The invention will be further described in conjunction with the accompanying drawings, in which:

FIG. 4A is a plan view of an alternate embodiment of a ring antenna utilized in conjunction with the uterine monitor of FIG. 1;

DETAILED DESCRIPTION OF THE PREFERRED EMBODIMENT

Figure 1:
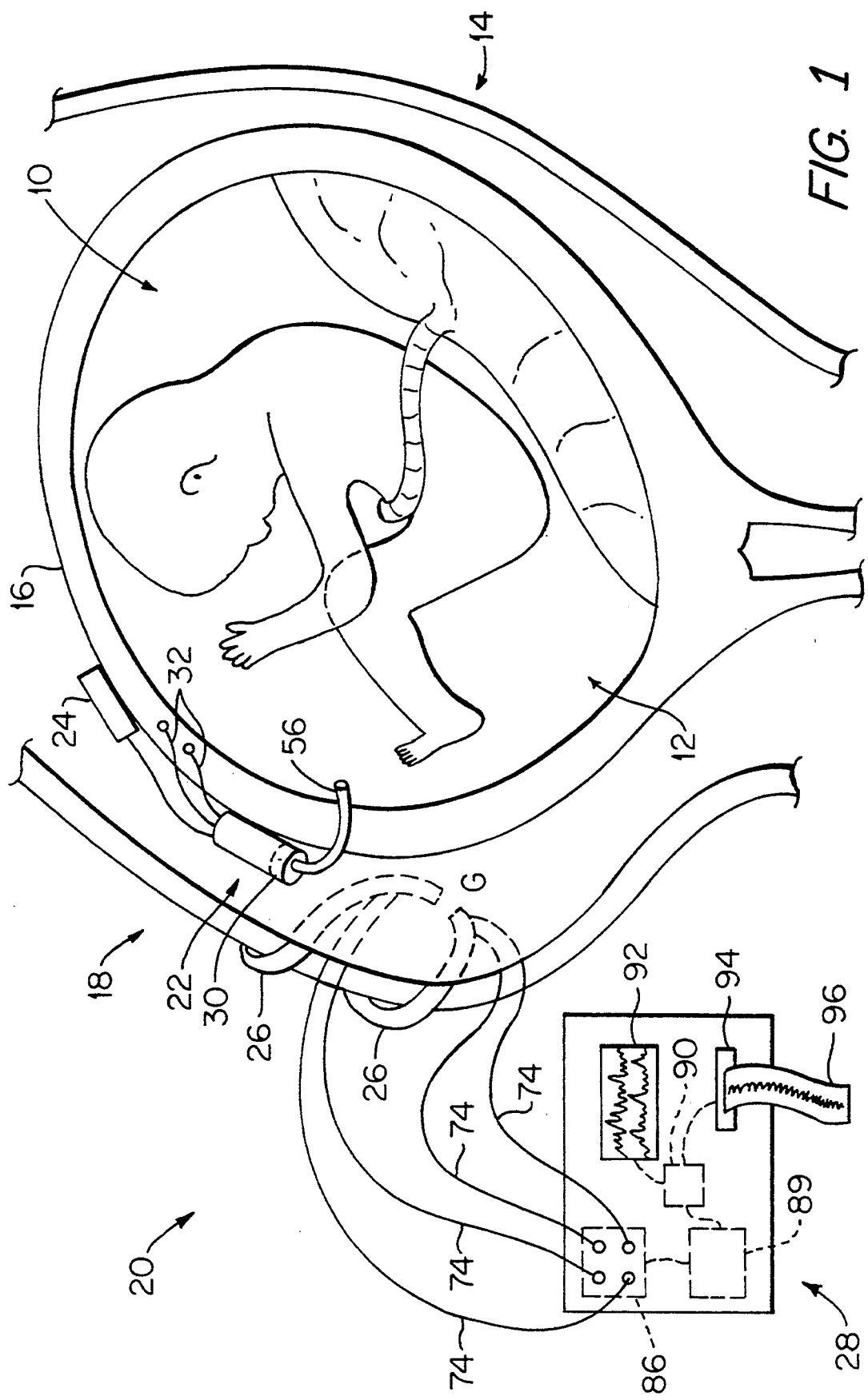
FIG. 1 is a cross sectional view of a fetus in a uterus having an attached uterine monitoring and medication delivery system constructed in accordance with a preferred embodiment of the invention.

With reference to the figures, wherein like reference characters indicate like elements throughout the several views and, in particular, with reference to FIG. 1, a fetus 10 is disposed within a uterus 12 of a mother 14. The uterus 12 is defined by a uterine wall 16 which is located within an abdominal wall 18 of the mother 14. A uterine monitoring system, generally denoted 20, is provided to monitor the status of mother 14 during an intra-operative or postoperative period as well as during the onset of parturition. The uterine monitoring system 20 comprises an implantable remote sensing unit 22, a medication dispenser 24, an antenna 26, and a monitor 28.

Remote Sensing Unit

The remote sensing unit 22 is a remote sensing device which detects maternal temperature and uterine electromyogram. The remote sensing unit 22 will also detect intra-uterine pressure by a pressure transducer 30.

The remote sensing unit 22 is secured to the uterine wall 16 by at least one electromyogram lead 32 or by a suture tab located on the body of the sensing unit 22. This lead is surgically inserted into the uterine wall 16 and will be discussed in detail below.

Figure 2:
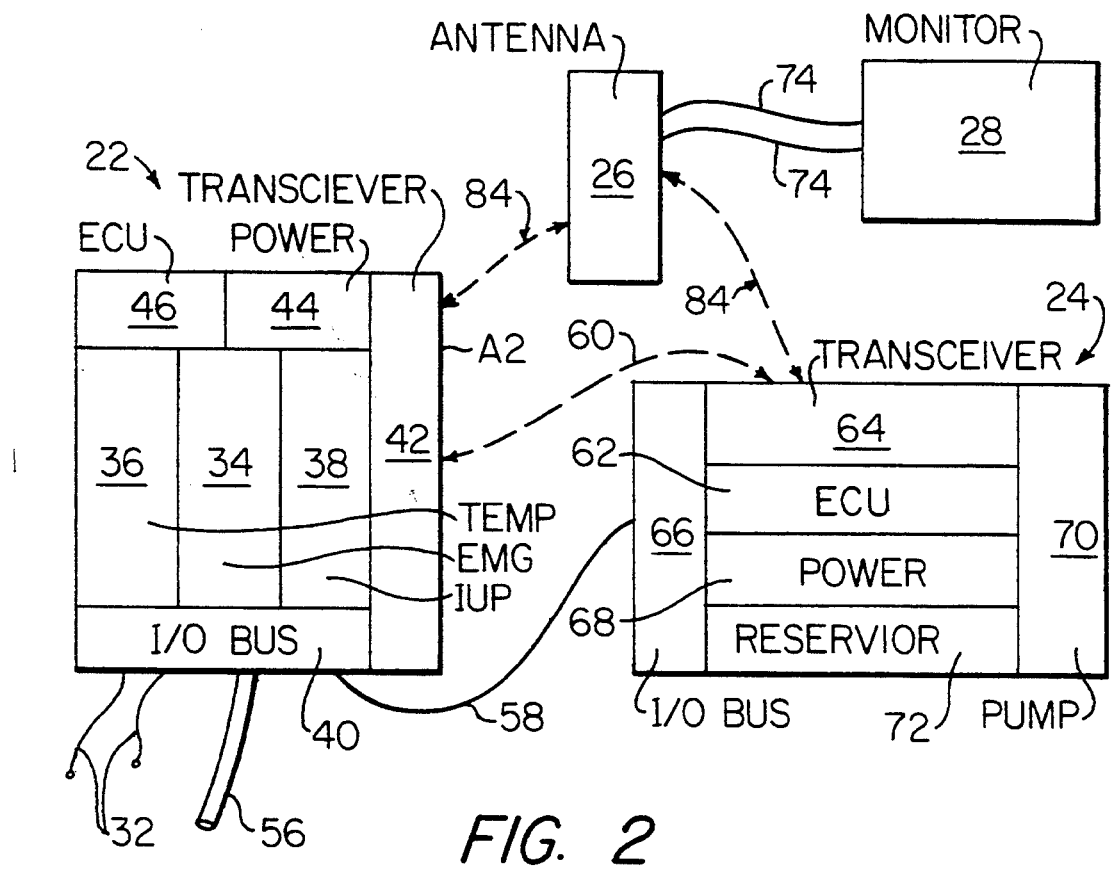
FIG. 2 is a block diagram of the components of the uterine monitor and medication delivery system of FIG. 1.

Referring to FIG. 2, a block diagram of the major components of remote sensing unit 22 are illustrated. As may be seen, circuitry for an electromyogram (EMG) 34, a temperature (Temp) sensor 36 and an intra-uterine (IUP) 38 sensor are provided within remote sensing unit 22. Information is transmitted to and from sensors 34, 36 and 38 via an input/output (I/O) bus 40. I/O bus 40 also provides communication between a transceiver 42 and sensors 34, 36 and 38. Power is supplied by a conventional power source 44 such as a silver oxide battery or any other power source known in the art. An electronic control unit (ECU) 46 is provided for controlling the power supply to sensors 34, 36 and 38, as well as communication through I/O bus 40 and transceiver 42. Each of the components of the remote sensing unit 22 will be described in detail below.

Figure 3A:
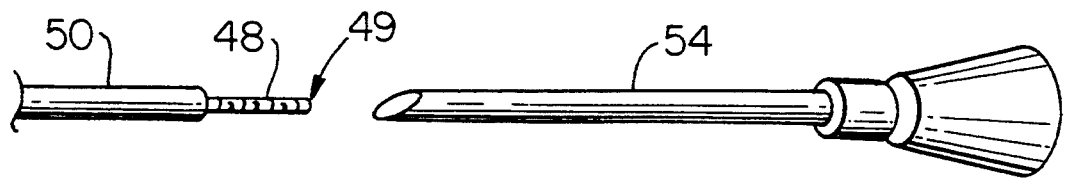
FIG. 3A is a side elevational view of an electromyogram lead utilized in conjunction with the uterine monitor of FIG. 1.

The electromyogram sensor 34 includes at least one electromyogram lead 32 which is affixed at a proximal end to a conventional signal processing circuit and at the distal end to the uterine wall 16. In the preferred embodiment, there are two electromyogram leads 32, the first affixed to the anterior uterine wall and the second affixed within 1 cm from the first. Referring to FIG. 3A, an electromyogram lead 32 is illustrated. The electromyogram lead 32 is formed from an inner conductive material 48 having a distal tip portion 49 and an outer insulative sheathing 50 which surrounds conductive material 48. The distal tip portion 49 of conductive material 48 is exposed to allow for an electromyogram signal to be transmitted along lead 32.

In conventional electromyogram leads, this distal tip portion 49 is left exposed to the environment. Having an exposed tip portion 49 creates significant problems when lead 32 is used in uterine monitoring. This exposed tip portion 49 may short-circuit the electrical circuit attached to the proximal end of lead 32 since lead 32 may be exposed to amniotic or other body fluids.

Figure 3B:
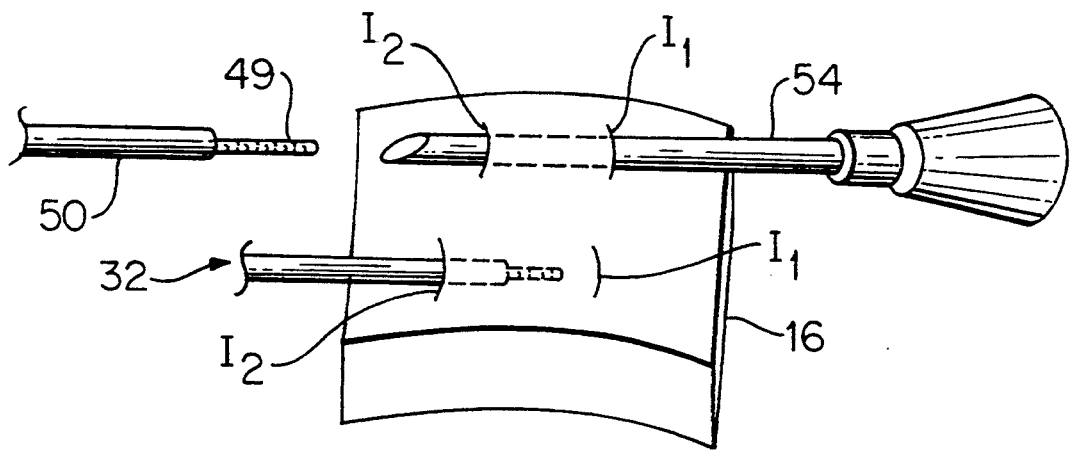
FIG. 3B is a side elevational view of the electromyogram lead of FIG. 3A as installed by the preferred method of the invention.

This invention contemplates a method for surgically installing lead 32 to prevent the possibility of, a short circuit or electrical shock and is described with reference to FIGS. 3A and 3B. An incision or needle hole $I_1$ is made in the uterine wall 16 wall of mother 14. Incision $I_1$ is wide enough to allow a hollow needle 54 to be inserted in and parallel to the uterine wall 16. A second incision or needle hole $I_2$ is made to allow for the insertion of tip 49 into the hollow needle 54. Finally, the needle 54 is slowly withdrawn as lead 32 is fed into incision $I_2$. This is continued until needle 54 is removed from incision $I_1$ and the tip 49 is disposed in the uterine wall 16. Finally, incisions $I_1$ and $I_2$ may be sealed by conventional sutures in a conventional fashion. Thus, the tip of lead 32 is maintained within the uterine muscle wall and is prevented from coming into contact with amniotic or body fluids. This method of subcutaneously implanting lead 32 reduces the risk of a short-circuit as well as that of electrical shock. While in a preferred embodiment the incision $I_1$ and $I_2$ are made in the anterior uterine wall, it is within the contemplation of this method to provide any entry and exit point for needle 54.

In a similar fashion, the above process is repeated for positioning and securing each lead 32 to the uterine wall 16. After all leads are secured, remote sensing unit 22 is attached to the proximal ends of each respective lead 32 and thus remote sensing unit 22 is firmly secured to the outer surface of the uterine wall 16 of mother 14 by leads 32 or conventional sutures and suture tabs. Electromyogram data is gathered in a conventional fashion and may be in either analog or digital form. It should be appreciated that the remote sensing unit 22 may be disposed on the uterine wall 16 or below the abdominal wall 18 of mother 14 or other implant site.

The temperature sensor 36 and associated signal processing circuit are an integral part of remote sensing unit 22. The sensor 36 is maintained in contact with the outer uterine wall 16 of mother 14 by remote sensing unit 22 and associated leads 32. Temperature information is gathered in a conventional fashion and may be in either analog or digital form. In an alternative embodiment, the above described temperature sensor 36 will utilize a sensor which is disposed remotely from remote sensing unit 22. If the remote sensing unit 22 is placed subcutaneously below the abdominal wall 18, then temperature sensor 36 will be placed in contact with uterine wall 16. The prior art has failed to provide accurate temperature measurements of the uterus of the mother 14 during the onset of parturition.

The importance of accurately measuring the temperature of a mother to determine the onset of parturition has been appreciated by the prior art but no system has been developed to continually monitor the uterine temperature of a mother 14 to determine a baseline temperature and to determine the onset of parturition based upon a drop in temperature from that baseline.

The pressure sensor 38 comprises a pressure transducer 30 and an electronic circuit for signal processing, both of which are located within remote sensing unit 22. Additionally, a pressure transmission catheter 56 is disposed externally to remote sensing unit 22 and is connected thereto for providing fluid communication between transducer 30 and uterus 12. As may be seen in FIG. 1, catheter 56 is disposed through uterine wall 16 so as to allow fluid communication between amniotic fluid, contained within uterus 12, and pressure transducer 30. It should be appreciated that a solid state pressure sensor such as that used in pressure sensing pacemakers which measure incremental changes in pressure with respect to time, i.e., dp/dt, as well as instantaneous pressure may be utilized in place of the sensor 38, described above. This will eliminate the need for the pressure transmission catheter 56 and thus reduce the problem of sterilizing the equipment. Additionally, it should be appreciated that a dual lumen catheter, such as that produced by Data Sciences of Minnesota, which utilizes pressure transducer 30 and a gel may be employed. This structure has the advantage of maintaining accurate measurements without requiring periodic flushing. Finally, fiber optic, capacitance, semiconductor strain gage, or any other type of pressure measuring device may be employed in sensing unit 22 in place of pressure transducer 30.

An I/O Bus 40 is provided for allowing for interoperability between sensors 34, 36 and 38 and transceiver 42. In a preferred embodiment, I/O bus 40 will be a simple one way communications line having buffers for data storage. It should be appreciated that a more complex I/O bus may be used in conjunction with a complex ECU 46 for providing additional features such as duplex communication, multiplexing or encoding. In a preferred embodiment, the I/O bus will have a communications line 58 for allowing information from sensors 34, 36 and 38 as well as control information from ECU 46 to be relayed to medication dispenser 24. Communications line 58 may be a standard copper wire or fiber optic cable. It should be appreciated that communication between remote sensing unit 22 and medication dispenser 24 may be accomplished by a radiotelemetry signal 60 between respective transceivers 42 and 64. This radiotelemetry signal is indicated in FIG. 2 as dashed line 60.

As mentioned above, remote sensing unit 22 contains a transceiver 42. Transceiver 42 is a combination of a radio transmitter and receiver which is maintained in a common housing and employs common circuit components for both transmitting and receiving radio signals. In a preferred embodiment, the bandwidths of the radio signals are within that of traditional radio-telemetry devices. As mentioned above, transceiver 42 receives sensor data from the I/O bus 40 and then in turn transmits this sensor data to either an external antenna 26 or to a medication dispenser 24. It should be appreciated that any frequency band may be employed for the transceiver so long as each band is unique to each particular transceiver 42 and each band is within the Federal Communications Commission (FCC) specifications. This is vitally important since there may be more than one patient being monitored at any one time. Additionally, in an alternative embodiment, the frequency band used to communicate with the medication dispenser 24 will be different from that of the antenna 26. As may be seen, communication between remote sensing unit 22 and medication dispenser 24 may be conducted via a radio transmission channel indicated by dashed line 60 or by a more conventional communications line 58.

Power is provided to the above components by a conventional power source 44. It should be appreciated that since the normal term of a mother 14 is approximately nine months, the power source 44 should be able to provide continuous power to the above systems for that time period. Currently, silver oxide batteries are utilized which provide power for at least four months. Power distribution may be controlled by the ECU 46 so that sensors 34, 36 and 38 may be selectively actuated when required and thus conserving the power supply from source 44.

The ECU 46 may be a conventional microcontroller which controls the communication along I/O bus 40 and power distribution as described above. For example, a known controller such as that described in Med. Progr. Technol. 9,17–25 (1982) may be utilized. Additionally, the microcontroller may be modified by pre-programming to automatically respond to particular characteristics which are detected by sensors 34, 36 and 38. In this case, the microcontroller may activate medication dispenser 24 to allow for treatment to be automatically delivered.

All external components of the remote sensing unit 22 will be coated with a thin layer of silicone or encased in a biocompatible case to allow for biocompatibility between unit 22 and mother 14. This reduces the possibility of infection or rejection of remote sensing unit 22 by mother 14.

Medication Dispenser

Turning now to the medication dispenser 24, as illustrated in FIG. 2, the major components of the medication dispenser 24 may be seen. The medication dispenser 24 comprises an electronic control unit (ECU) 62, a transceiver 64, an I/O bus 66, a power supply 68, a pump 70, and a medication reservoir 72. Elements 62, 64, 66, and 68 correspond to elements 46, 42, 40, and 44 respectively and function similarly. Therefore, only the differences in these elements will be discussed below.

As mentioned above the ECU 62 is similar to that of ECU 46. It should be appreciated that either ECU 46 or 62 is capable of automatically responding to particular characteristics which are detected by sensors 34, 36 and 38. Thus, if one ECU is provided with this feature, the other may have this feature deactivated. Alternatively, a comparator circuit may be provided to determine if both ECUs 46 and 62 agree on the response to the particular condition. In that case, medication dispenser 24 will only be activated if both ECUs 46 and 62 agree. Otherwise, an error signal will be sent to monitor 28 via antenna 26. Another major difference between ECUs is that ECU 62 will have to determine which reservoir 72 to physically connect to pump 70. This may be accomplished via conduits and electromagnetically controlled valves or any other valve means known in the art.

Pump 70 is preferably a piezoelectrically driven micro-pump generally similar to that described by Rosenberg et al. in U.S. Pat. No. 4,596,575. In the preferred embodiment, pump 70 will only be required to dispense liquid medication. In an alternate embodiment, pump 70 may be modified to allow for dispensing of sold or powdered medications as well as liquids.

Finally, at least one reservoir 72 is provided for maintaining the medications. In a preferred embodiment, each reservoir 72 comprises a collapsible bag which is maintained within a rigid housing of medication dispenser 24.

As mentioned earlier, data from sensors 34, 36 and 38 are provided to medication dispenser 24 by remote sensing unit 22 via either a communications line 58 or a radio transmission channel 60. In an alternative embodiment, medication dispenser 24 will be provided with independent data sensors. All external components of medication dispenser 24 will be coated with a thin layer of silicon to allow for biocompatibility between dispenser 24 and mother 14. This reduces the possibility of infection or rejection of medication dispenser 24 by mother 14.

It should be appreciated that no known references have suggested the direct medical treatment of a mother 14 during pregnancy by an automatic medication dispenser 24.

While the prior section has discussed the gathering of data and the value of this data, the next section shall discuss how that data is transmitted and manipulated in devices located outside of the mother 14.

Antenna

Figure 4B:
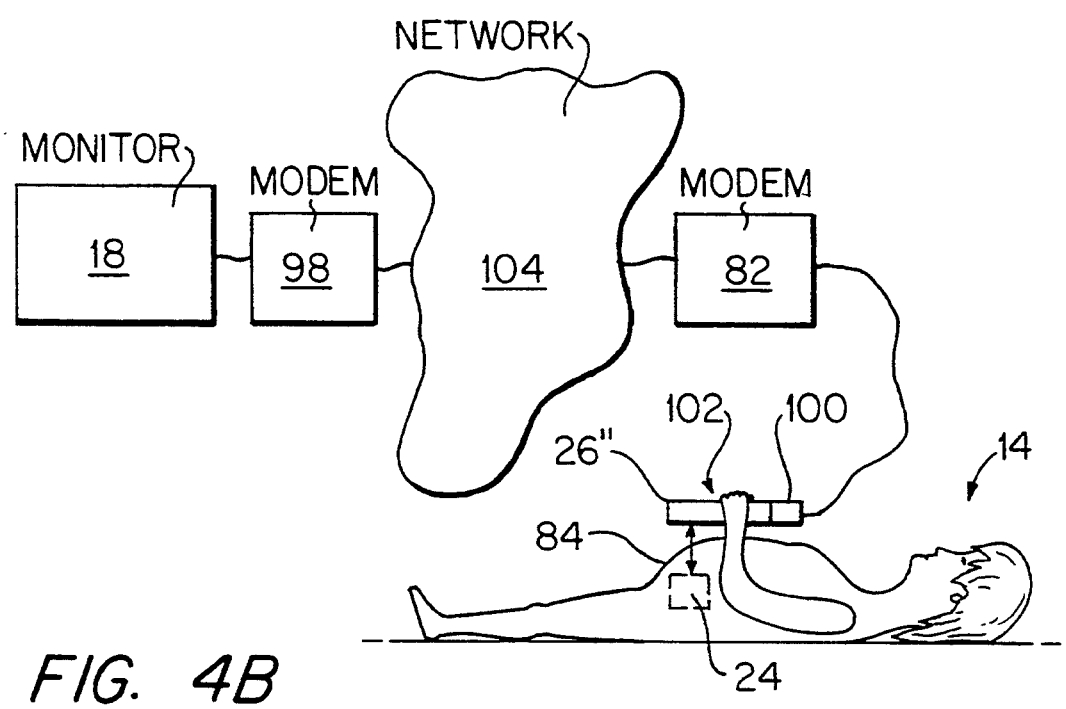
FIG. 4B is a block diagram of an alternate communications method utilized in conjunction with the uterine monitor of FIG. 1.
Figure 4C:
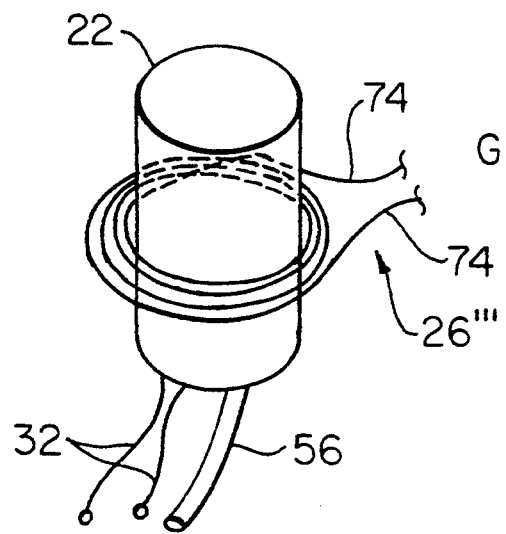
FIG. 4C is a perspective view of an alternate embodiment of a ring antenna utilized in conjunction with the uterine monitor of FIG. 1.

As mentioned earlier, the ECG, temperature and intra-uterine pressure information is transmitted from transceiver 42 by the use of a standard radio-telemetry signal 84 to an external monitor or control unit 28. This is accomplished by the radio-telemetry signal 84 being received by an antenna 26. There are four types of antennas 26 which are specifically contemplated by the invention. The first type of antenna 26 is a flexible loop antenna and is illustrated in FIG. 1 as element 26. The second type of antenna is a ring retractor antenna and is illustrated in FIG. 4A as element 26'. The third type of antenna is a wand or tubular antenna and is illustrated in FIG. 4B as element 26". The fourth type of antenna is a small contact loop antenna attached directly to the sensing unit 22 and is illustrated in FIG. 4C as element 26'''. Each of these antennas 26, 26', 26" and 26''' shall be discussed in detail below.

The flexible loop antenna 26 is formed from a conductive ring or band of material which is placed around the abdominal wall 18 of the mother 14. In a preferred embodiment, loop antenna 26 will be formed from several conductive rings or bands which are interwoven. This may be more clearly pictured as several coils of wire which are compressed together. As may be seen in FIG. 1, a gap G is provided in the last coil of loop 26 to allow for a continuous electrical circuit to be formed between loop antenna 26 and monitor 28. Electrical leads 74 are attached to respective ends of gap G and are provided to allow an electrical connection between antenna 26 and monitor 28. For clarity only four electrical leads 74 have been illustrated in FIGS. 1, 2 and 4A. It should be appreciated that the number of electrical leads 74 will correspond to the number of monitored characteristics or sensors utilized in the fetal monitoring system 20. In a multiplexed system, there will only be one electrical lead 74. This ring structure is the preferred antenna 26 structure for both intra-operative and postoperative periods since the antenna 26 is capable of receiving a signal from any position within the mother 14, i.e., omnidirectional. Additionally, the antenna 26 may be bent to any shape. due to the malleable nature of the conductive rings, and thus may be bent to conform to the shape of the mother's abdomen 18.

The ring retractor antenna 26' which is illustrated in FIG. 4A comprises a conventional ring retractor such as that disclosed by Gauthier in U.S. Pat. No. 4,010,741. The conventional ring retractor is modified by providing a gap G in a conductive ring 76 for allowing a continuous electrical circuit to be formed between ring retractor antenna 26' and monitor 28. Electrical leads 74 are attached to respective ends of gap G for providing an electrical connection between antenna 26' and monitor 28. Additionally, there are a plurality of arms 78, each of which is secured to ring 76 and supports an associated retractor 80. The ring retractor antenna 26' functions in a similar fashion to a conventional ring retractor but also provides the ability to receive sensor information from transceivers 42 and 64 via radio-telemetry signal 84. This antenna 26' has the advantage of not increasing the number of additional devices which are present during an operation and thus, is the best choice for intra-operative monitoring. For best results, antenna 26' is used in conjunction with antenna 26 to receive an accurate radio-telemetry signal from transceivers 62 and 64.

In a similar fashion as loop antenna 26, a small contact loop antenna 26''' is illustrated in FIG. 4c. This contact antenna 26''' is fastened in a similar manner as loop antenna 26 except it is much smaller in size, i.e., approximately 1-2 cm diameter loop. The contact antenna is designed to be used during an interoperative period and is placed around and in contact with sensing unit 22. The antenna 26''' is attached to a wire lead 74 which is attached to monitor 28.

Finally, a wand or finger antenna 26" may be utilized in particular circumstances. The finger antenna 26" is a unidirectional antenna and thus is more limited than the flexible loop antenna 26. Antenna 26" is useful for postoperative monitoring of both fetus 10 and mother 14. In a preferred embodiment, this finger antenna 26" is provided with an RJ-11 jack and associated signal processing circuitry at a distal end to allow antenna 26" to be attached to a conventional modem 82. Thus, while a mother 14 is at home, her doctor may receive sensor information at a remote site. This communication system is discussed in greater detail below.

It should be appreciated that a combination of the above antennas may be utilized to provide the best data signal to monitor 28. Additionally, the purpose of antenna 26", illustrated in FIG. 4, may be achieved by using either antenna 26, 26' or 26''' in place of antenna 26". Finally, it should be appreciated that any known antenna which may receive frequencies in the frequency ranges of conventional radio-telemetry devices may be utilized in place of any of the above identified antennas.

Monitor

Turning back to FIGS. 1 and 5, a generic monitor 28 is illustrated. Monitor 28 includes a signal input means 86; a receiver 89 for processing the signal from input means 86; a computing means 90; and output means for visual or printed displays 92 and 94, respectively. In a preferred embodiment, the signal input means 86 is a patch panel which utilizes standard banana connectors affixed to electrical leads 74. Signals from input means 86 may be processed by a receiver, model CTR-86-SA-OPO7 and model BCM-100 consolidated matrix, produced by Data Sciences of St. Paul, Minn. and distributed by Mini-Mitter Co. of Sunriver, Oreg. The signal received from any antenna 26 can be processed in several ways. Early trials utilized a CTR-86 which had only electrocardiogram or electromyogram and temperature outputs. The signal output was an analog ECG or EMG and a voltage which corresponded to the temperature. The computing means 90 was Hewlett-Packard Vectra Model 50 which is produced by Hewlett-Packard Co. of Sunnyvale, Calif. The computing means 90 further comprises a 10 MHz 80287 math coprocessor produced by Intel Corp. of Hillsboro, Oreg. and a DQ-1088 data acquisition card produced by Data Sciences, Inc. of St. Paul, Minn. Unfortunately this device was exceedingly clumsy and unreliable.

In a preferred embodiment pressure measurements are also taken. The transmitted multiplexed signal, i.e. the EMG, temperature and pressure is received by any of several antennas 26 described above and decoded by one of several receivers produced by Data Sciences, e.g., RLA 3000. Further signal processing and digital to analog conversion is performed by a DL10 decoder with analog (voltage) outputs by A10, A11 and A12 options. These analog signals are then processed by the computing means 90, e.g., a Macintosh 950 computer. The computing means 90 is also equipped with a National Instruments NB-M10-16 I/O board and a national Instruments NB-DMA 2800 interface board.

A computer based data acquisition system software package LabView, Version 2.2.1, is operated within computing means 90 for manipulating the data to determine the health of mother 14. This software package has been specifically modified to detect conditions such as fetal distress, hypothermia, and the onset of parturition. The application of these modifications are discussed below in conjunction with the overall operation of the fetal monitor 20.

Output from the computing means 90 may be displayed on a visual display means 92 such as a cathode ray tube (CRT), liquid crystal display or any other display means known in the art. Additionally, output from computing means 90 may be displayed on a strip chart recorder 94 such as Model MT 9500-0R produced by Coulbourn Instruments of Lehigh Valley, Pa. This strip chart. recorder 94 allows for the simultaneous real time display of maternal temperature and recording of analog maternal electromyogram on a strip chart 96.

Additionally, a continuous real time display 92 of the electromyogram signal may be performed using any monitor capable of displaying electrocardiograms. In a preferred embodiment, a Lifepak Six produced by Physio-Control, of Redmond, Wash. is utilized.

For postoperative patient transport, the system has been modified to be mobile and battery powered. This involves modifying the receiver and decoder, described above, to function on a 9 volt battery and utilizing a transport monitor similar to the Lifepak Six.

Fetal Monitor

Figure 5:
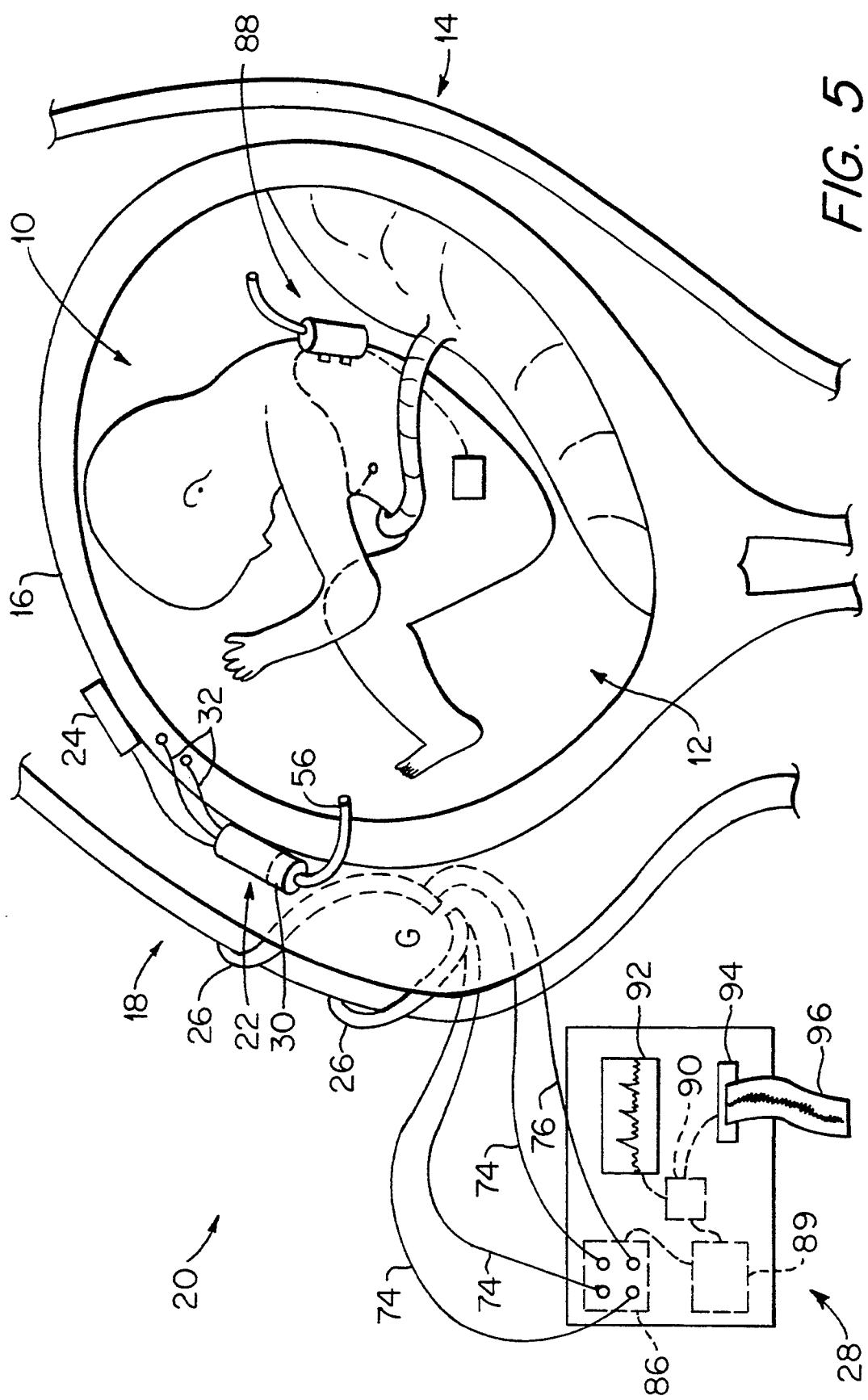
FIG. 5 is an alternate embodiment of the uterine monitor of FIG. 1.

Referring to FIG. 5, an optional fetal monitor 88 is illustrated in conjunction with the uterine monitor 22. Fetal monitor 88 provides information such as fetal temperature, fetal heartrate, and fetal electrocardiogram to monitor 28. Additionally, pressure transducer 30 may be placed in the fetal monitor 88 instead of the uterine monitor 22. For a complete discussion of the fetal monitor 88, please see co-pending U.S. application Ser. No. 08/081,139 which is hereby incorporated by reference.

Operation of Device

Turning now to the operation of the uterine monitoring system 20 in conjunction with the fetal monitor 88, reference is made to FIGS. 6A, 6B, 7, 8, 9, and 10A–10D. As stated earlier, uterine monitor 22 is designed for use during intra-operative and postoperative periods as well as during the onset of parturition or labor.

Figure 7:
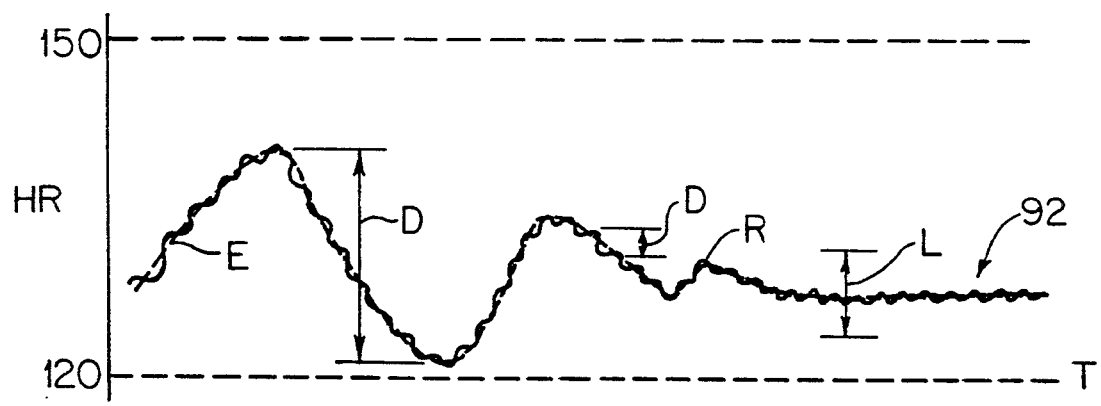
FIG. 7 is a plot of fetal heart rate versus time.
Figure 8:
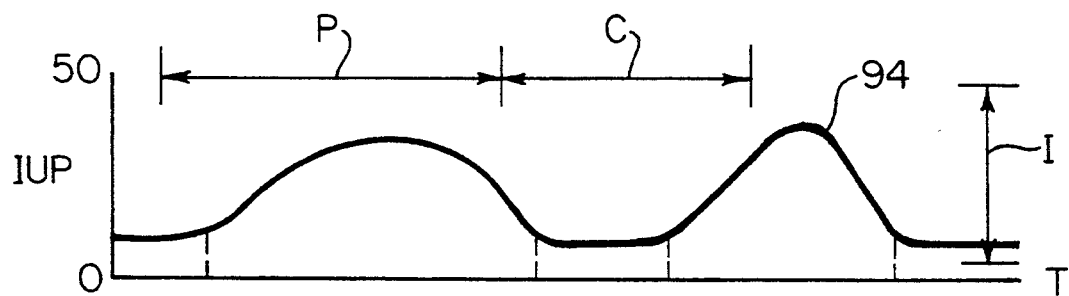
FIG. 8 is a plot of intra-uterine pressure versus time.
Figure 9:
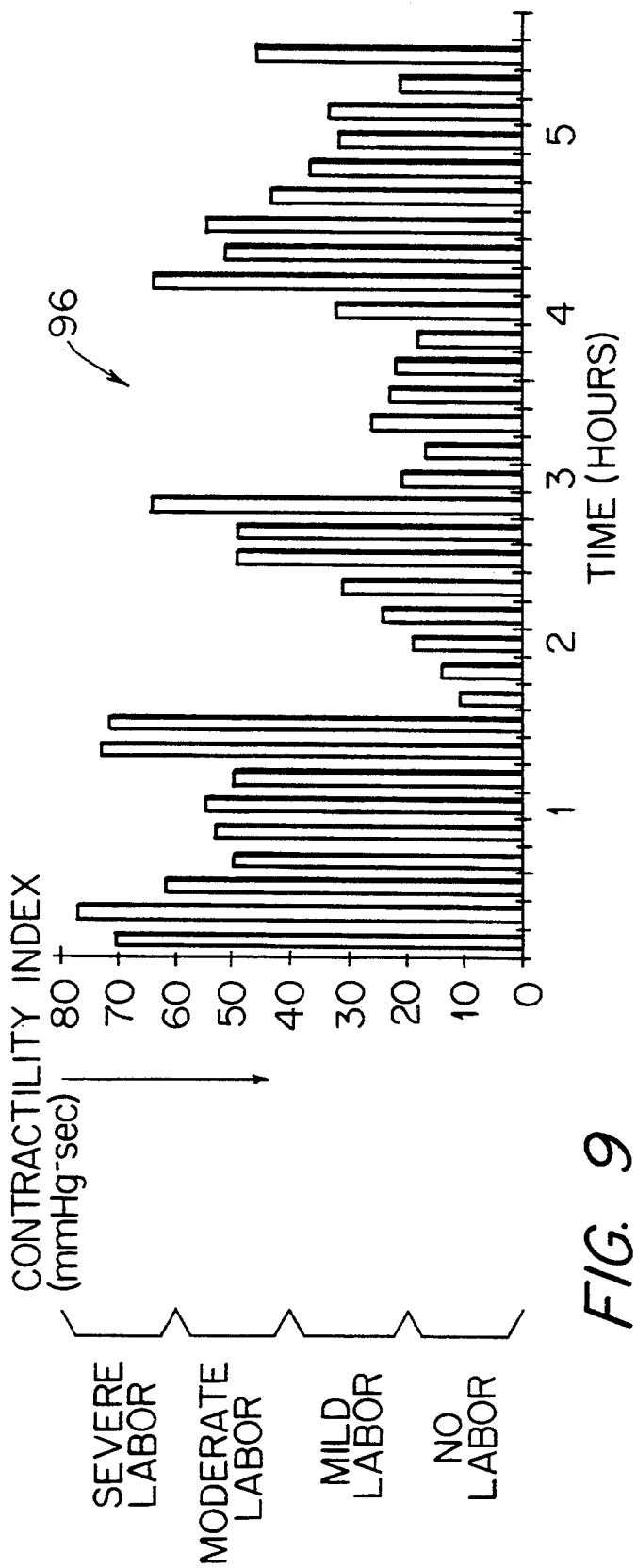
FIG. 9 is a plot of uterine contractility index versus time.

During the onset of parturition or labor, the uterine monitor 20 will monitor a maternal electromyogram signal 91 as illustrated in FIGS. 10A through 10D and may monitor maternal heart rate, generally denoted 92 in FIG. 7. During parturition, muscles in the uterine wall generate ion fluxes during cell depolarization which in turn lead to cellular contractions. This may be detected as changes in voltage across a portion of the muscle and is generally called an electromyogram. The voltage detected corresponds to a muscular contraction. The electromyogram signal 91 is first detected by electromyogram leads 32. These leads 32 relay signal 91 to electromyogram sensor 34 which in turn provides signal processing such as noise reduction and amplification to signal 91 as described above. Signal 91 is then transmitted by transceiver 42 to antenna 26 or transceiver 64 as described above. It should be appreciated that maternal electrocardiogram ECG and heart rate may be measured by standard skin ECG leads but the uterine electromyogram signal 91 may not.

Once signal 91 is received by antenna 26, signal 91 is then transmitted to monitor 28 via electrical leads 74. This electromyogram signal 91 provides an accurate indication of the beginning and end of a contraction. This information is essential for accurately determining the onset of parturition.

The generally accepted way to determine the progress of parturition is to time the interval between contractions. This method, while indicative of the general onset of parturition, is highly inaccurate for determining the exact progress of parturition and may be totally inaccurate due to false labor pains. Since the onset of labor pains are brought on by contractions, the measurement of contraction intervals is only one information source. The intensity of the contractions is another vital source of information in the determination of parturition. In the past, this intensity information was provided as a qualitative measurement by the mother to the health care professional. Thus the prior art does not disclose a quantitative method for measuring the intensity of uterine contractions as described above nor does it disclose an accurate method of determining the beginning or end of a contraction.

While this electromyogram information is indicative of parturition, false alarms may be generated. Therefore intra-uterine pressure is also utilized in the determination of parturition.

In a preferred embodiment of the invention, intra-uterine pressure is measured by a pressure transducer as described above. This information is then transmitted to monitor 28 in a fashion similar to that of the electromyogram signal 91. As may be seen in FIG. 8 and 10A though 10D, curves of intra-uterine pressure 94 are illustrated. There are several characteristics which may be determined from the intra-uterine pressure. The duration or period P of a contraction may be determined by the fluctuation in intra-uterine pressure over a time period T. The time between contractions, indicated as C, may also be measured. Finally, the intensity of contractions I may be determined. Based upon any one these or preferably a combination of the above, the onset and progress of parturition may be determined. In a preferred embodiment, the integral of the intra-uterine pressure taken over ten minute intervals is utilized to generate a contractibility index, generally denoted 96 in FIG. 9. The contractibility index 96 allows for the graphical representation of the progress of parturition. A medical professional may determine whether the contractions are indicative of a false labor or are actually the onset of parturition. As may be seen in FIG. 9, the contractility index may be broken up into four discrete regions, severe labor, moderate labor, mild labor and no labor. A medical professional may determine how far along the patient is by the magnitude of the last contractibility index reading. This is vitally important for determining if and when to perform a caesarean section, or for the administration of medication. In a preferred embodiment, a ten minute time period is utilized for determining the index values but it should be appreciated that any time interval may be utilized.

Figure 6A:
FIG. 6A is a plot of maternal electrocardiogram versus time.
Figure 6B:
FIG. 6B is a plot of fetal electrocardiogram versus time.

Additionally, fluctuations in intra-uterine pressure may be used to provide corrections to both the fetal electrocardiogram and maternal uterine electromyogram signals. The maternal electrocardiogram signal is illustrated in FIG. 6A as curve 93. These electromyogram and electrocardiogram signals are utilized to determine the health of both fetus 10 and mother 14 and the onset of parturition.

As may be seen form FIGS. 10A through 10D, there is a close correlation between increasing intra-uterine pressure and increases in electromyogram. This collaborates the theory that the myometrium contractions are causing the increase in intra-uterine pressure as opposed to application of an external force such as a situp, a hand pushing on the abdomen or possibly even gastric digestion. Thus, by correlating the intra-uterine pressure information with that of the electromyogram, false indications of labor are reduced.

Turning now to the use of the temperature information, maternal temperature also may be measured in a similar fashion to that described for the electromyogram signal 91. As indicated above, there is a correlation between a drop in temperature of fetus 10 and mother 14 and the onset of parturition. While the prior art has suggested this correlation, it has failed to provide an accurate way of determining uterine or fetal temperature. But temperature alone is not a good indicator of the onset of parturition. The combination of temperature, intra-uterine pressure and electromyogram data provide the most accurate indication of the onset of parturition. This is because there must be a temperature drop in conjunction with elevated intra-uterine pressure and electromyogram response. It should be appreciated that the prior art neither teaches or suggests the monitoring of these three characteristics for determining parturition.

Additionally, the invention contemplates the concept of monitoring maternal heart rate variability. The maternal heart rate variability 92 may be determined as illustrated in FIG. 7. For clarity of discussion, only the maternal heart rate will be discussed in detail. It should be appreciated that fetal heart rate variability may also be measured in a similar way.

As may be seen from FIG. 7, heart rate variability has both long term and short term characteristics. The long term characteristics are represented by the envelope D of heart rate curve 92 and the short term characteristics being shown by the ripple R about the envelope E. Envelope E represents a straight line approximation of the actual heart rate 92. In a alternate embodiment, parturition is determined from the weighted average of the peak to peak distance D in the instantaneous heart rate curve 92, i.e. long term variability in heart rate. Parturition also may be determined by the variability in short term heart rate as indicated by the distance D'. Finally, parturition may be determined if predetermined minimum peak to peak limits L are exceeded within a given period of time. It should be appreciated that a combination of the above methods may be employed. While this heart rate information is indicative of parturition, false alarms may be generated. Therefore intra-uterine pressure is also utilized in the determination of parturition.

Figure 10A:
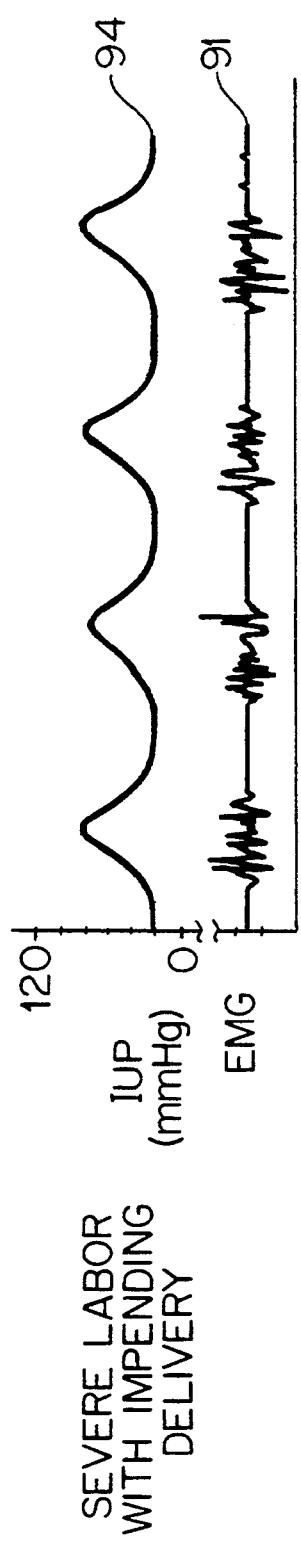
FIGS. 10A, 10B, 10C and 10D are plots of maternal intra-uterine pressure and electromyogram versus time for severe, moderate, mild and no labor, respectively.
Figure 10B:
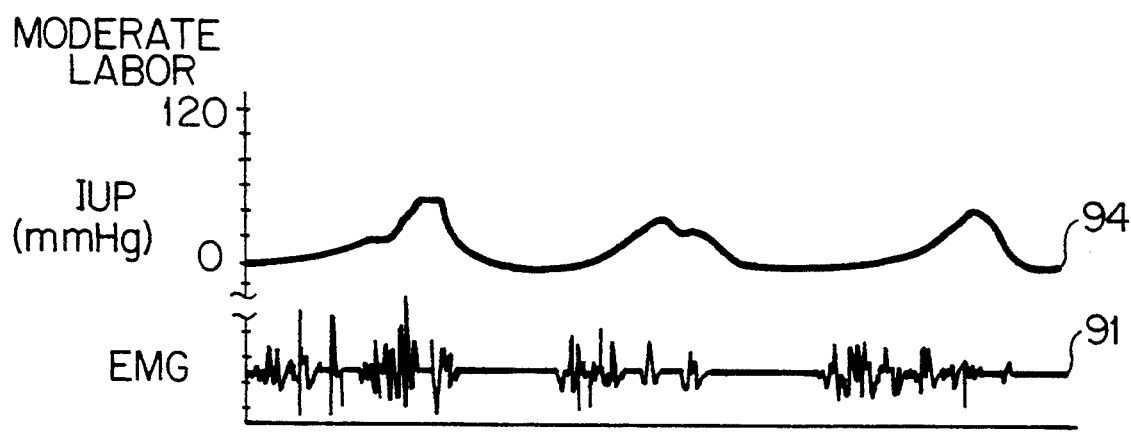
Figure 10C:
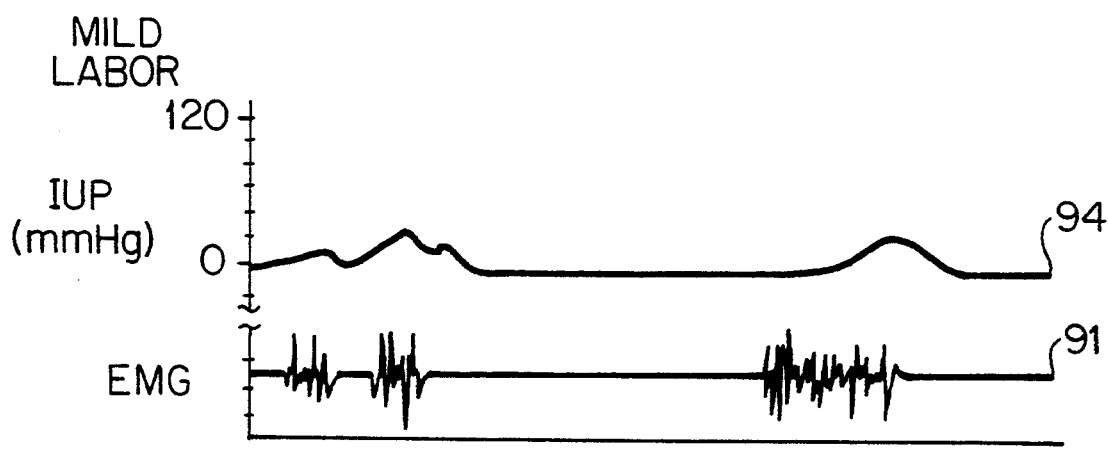
Figure 10D:
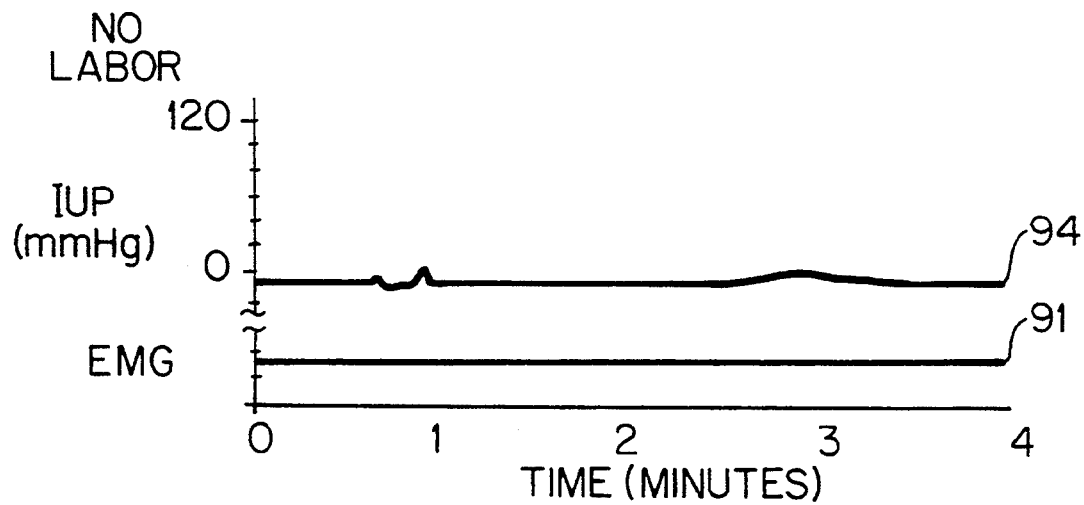

These signals in combination with the temperature pressure and electromyogram signals may be utilized to automatically administer drugs from medication dispenser 24 for aiding, slowing or inhibiting the labor process as described above. FIGS. 10A through 10D illustrate the progressive effect of injecting a mother with labor inhibiting drugs of increasing dosages. As may be seen in FIG. 10A the patient is in severe labor with impending delivery. By injecting the patent with a labor inhibiting drug, the doctor may slow the labor process to a moderate level or mild level as illustrated in FIGS. 10B and 10C, respectively. The doctor may even stop the labor process as indicated in FIG. 10D. The combination of intra-uterine pressure and electromyogram data provide an accurate indication of the onset of parturition. It should be appreciated that the prior art neither teaches or suggests the monitoring of both intra-uterine pressure and electromyogram data for the determination parturition. In fact, the prior art teaches away from utilizing this information for clinical monitoring. For example, see "Computer Analysis of Mechanical and Electrical Uterine Activity," by Ramondt et al. (1986).

Turning now to monitoring the mother and fetus during the intra-operative and postoperative periods, the measurement of fetal temperature and electromyogram as well as maternal temperature, intra-uterine pressure and electromyogram provide an accurate indication of the health of both mother 14 and fetus 10. The measurement of fetal temperature data is vital for determining the onset of hypothermia and for providing collaborative evidence of fetal distress, particularly during surgery. Fetal temperature will vary with time between upper and lower acceptable temperature limits. By measuring the temperature and determining when the temperature falls below preset limits, hypothermia may be determined quickly and automatically. Additionally, by seeing if there is a temperature variation in conjunction with a heart rate variation, fetal distress may be accurately determined.

Alternate Embodiment

In an alternate embodiment, implantable remote sensing unit 22' (not shown) is secured to uterus 12 and telemeters information to monitor 28'. Remote sensing unit 22' is similar to that of sensing unit 22 except that sensing unit 22' has been modified to minimize the functions and complexity in order to minimize physical size and maximize battery life. The small physical size of sensing unit 22 or 22' will allow surgical placement of and removal from mother 14 by using minimally invasive techniques. In this alternate embodiment, complex signal processing, detection and signalling functions are incorporated into monitor 28'. Monitor 28' is similar to that of monitor 28 except that it will carry out the above functions and will be able to be worn by the mother 14, or located nearby on a bedstand or purse and is discussed in detail below.

In this alternate embodiment, remote sensing unit 22' senses temperature, uterine electrical activity and intra-uterine pressure. Remote sensing unit 22' is secured to uterus 12 by a conventional suture and suture tab arrangement. Electromyogram leads 32 are inserted into or secured to the surface of uterine wall 16 as previously described above. Pressure transmission catheter 56 is positioned as previously described above. Signals from pressure sensor 38, uterine electrical activity sensor 34 and temperature sensor 36 are combined into one signal by a multiplexer (not shown). A transmitter 42', employing conventional circuit components, transmits the multiplexed signal by radio waves to monitor 28'. It should be appreciated that any subset of the pressure, uterine electrical activity and temperature may be sensed and transmitted in this embodiment.

Power is provided to the circuits of remote sensing unit 22' by a conventional power source similar to that of power source 44. It should be recognized that it is desirable for remote sensing unit 22' to have sufficient battery life to function continuously for up to two years. It is anticipated that patients will be implanted with a remote sensor 22' and that this sensor may remain in the patient for two or more pregnancies. It is therefore recognized that it is desirable to incorporate a conventional power switching mechanism (not shown) which will allow remote sensing unit 22' to be turned on and off remotely, without the need for surgical intervention. This power switching mechanism may be actuated by a magnetic field, an electromagnetic field or any other means known in the art.

Monitor 28' may incorporate an internal antenna 26'''' and receiver which will detect, amplify and process radio frequency transmissions from remote sensing unit 22' in a conventional manner. Alternatively, monitor 28' may employ any of the antenna structures 26, 26', 26'' or 26''' described in conjunction with the preferred embodiment. It should be recognized that monitor 28' should ideally be small enough to be worn by the mother 14 or placed in a purse or on a bedstand. Therefore monitor 28' will be substantially simpler than the monitor 28 of the preferred embodiment.

Signals from the receiver are directed to a signal processing unit (SPU). In one embodiment, the SPU employs a microcomputer program to process signals from the receiver in order to automatically detect or predict the onset or occurrence of labor. This program may process pressure, uterine electrical activity and temperature in combination or any subset thereof for the purpose of detecting labor as described in the preferred embodiment. A display means may be incorporated into monitor 28'. This display may be a liquid crystal display, audible means or both. Administration of medication by a medication dispenser 24' may be automatically controlled by the SPU as described in the preferred embodiment. In this embodiment, the medication dispenser 24' may be incorporated into monitor 28', may be placed in a separate housing, or may be surgically inserted into a patient as described in the preferred embodiment.

Alternative Monitoring

This system may allow monitoring of fetus 10 while mother 14 is away from the hospital. This is accomplished by interfacing a standard ECG monitor 28 to a modem 98 at the medical facility and having a corresponding remote unit at the mother's remote location. The remote unit comprises a second modem 82 corresponding to the medical facility modem 98; a transceiver 100 for transmitting and receiving information to modem 82, an antenna 26'' for receiving information from uterine monitor 22. In a preferred embodiment, transceiver 100 and antenna 26'' are maintained in a wand shaped housing 102. Optional signal processing circuitry for providing compatibility between the remote sensing unit output signals and the ECG input signals may be provided. By using the radio-telemetry device described above and a conventional ECG 28, the signal processing circuitry may be eliminated.

In operation, the radio-telemetry signal 84 is received by antenna 26'' as described above. Then, this signal is processed by conventional signal processing circuitry to generate a signal compatible with modem 82. Modems 82 and 98 are conventional in nature and allow communication across a network 104. It should be appreciated that network 104 may be a packet switched network, a conventional telephone line, a T1 network or any other communications network functioning with or without encryption. Once the signal is received by modem 98, it is converted to a format compatible with monitor 28 which functions substantially as described above.

Medical Trials

Five trials have been performed during congenital diaphragmatic hernia repairs on human fetuses 10. The fetal electromyogram and temperature were recorded accurately, and demonstrated that the system 20 functioned in the electrically noisy operating room environment. Of note from these tests was the failure of other intra-operative fetal monitoring techniques. The skin electrodes failed to detect fetal electromyograms and the fetal pulse oximeter failed altogether in one case.

Postoperatively, adequate close monitoring of electromyogram and temperature signals was maintained with the uterine monitoring device 20, described above, for over four weeks. Finally there were no complications associated with the uterine monitoring device 20.

Although the present invention has been fully described in connection with the preferred embodiment thereof with reference to the accompanying drawings, it is to be noted that various changes and modifications are apparent to those skilled in the art. Such changes and modifications are to be understood as included within the scope of the present invention as defined by the appended claims, unless they depart therefrom.

What is claimed is:

1. A uterine monitor for measuring characteristics indicative of labor said monitor comprising:
   means for sensing an intra-uterine pressure of a mother and for outputting a pressure signal;
   means for sensing uterine temperature and for outputting a sampled uterine temperature signal;
   means for sensing electrical activity of a uterine muscle of said mother's uterus and for outputting an electromyogram signal; and
   means for receiving said pressure, temperature and electromyogram signals and for determining the onset of labor based upon said pressure, temperature and electromyogram signals.

2. The uterine monitor recited in claim 1, wherein said means for sensing an electromyogram comprises:
   at least one electromyogram lead having an exposed distal end, said electromyogram lead for receiving electrical signals indicative of a maternal electromyogram;
   a noise reduction means secured to a proximal end of said electromyogram lead; and
   an amplification means for amplifying said electromyogram signal.

3. The uterine monitor recited in claim 2, wherein said exposed distal end of said electromyogram lead is maintained within a uterine wall of said mother for preventing accidental short circuits.

4. The uterine monitor recited in claim 1, wherein said outputting means for said electromyogram signal comprises a transceiver.

5. The uterine monitor recited in claim 4, wherein said transceiver is a radio-telemetry transceiver.

6. The uterine monitor recited in claim 1, wherein said means for sensing the intra-uterine pressure of said mother comprises:
   a pressure transducer; and
   a pressure transmission catheter for providing fluid communication between amniotic fluid contained in a uterus and said pressure transducer.

7. The uterine monitor recited in claim 1, wherein said outputting means for said intra-uterine pressure signal comprises a transceiver.

8. The uterine monitor recited in claim 7, wherein said transceiver is a radio-telemetry transceiver.

9. The uterine monitor recited in claim 1, wherein said means for receiving comprises an antenna.

10. The uterine monitor recited in claim 9, wherein said antenna is a ring retractor antenna.

11. The uterine monitor recited in claim 9, wherein said antenna is a flexible loop of conductive material.

12. The uterine monitor recited in claim 9, wherein said antenna is a finger antenna.

13. The uterine monitor recited in claim 1, wherein said determining means comprises:

a receiver for receiving said electromyogram and pressure signals;

a computing means; and an output means.

14. The uterine monitor recited in claim 13, wherein said computing means comprises a central processor, memory, arithmetic logic unit, and a communications bus for passing said electromyogram and pressure signals from said receiver to said output means.

15. The uterine monitor recited in claim 13, wherein said output means comprises a liquid crystal display.

16. The uterine monitor recited in claim 13, wherein said output means comprises a cathode ray tube.

17. The uterine monitor recited in claim 13, wherein said output means comprises a strip chart recorder.

18. The uterine monitor recited in claim 1, further comprising an automatic dispensing means for dispensing medication to said mother upon the onset of labor.

19. The uterine monitor recited in claim 18, wherein said automatic dispensing means comprises:

communications means for communicating with said determining means;

a pump for dispensing said medication;

a reservoir for maintaining said medication for said pump; and actuation means for receiving a signal from said communications means and for actuating said pump based upon said signal.

20. The uterine monitor recited in claim 19, wherein said communications means comprises a transceiver.

21. The uterine monitor recited in claim 20, wherein said transceiver is a radio-telemetry transceiver.

22. The uterine monitor recited in claim 19, wherein said pump is a piezoelectrically driven micro-pump.

23. The uterine monitor recited in claim 19, wherein said reservoir is a collapsible bag.

24. The uterine monitor recited in claim 18, wherein said automatic dispensing means comprises:

communications means for communicating with said outputting means for electromyogram signal and for communicating with said outputting means for pressure signal;

a pump for dispensing said medication;

a reservoir for maintaining said medication for said pump; and actuation means for receiving said electromyogram and pressure signals from said communications means and actuating said pump based upon said signals.

25. The uterine monitor recited in claim 1, wherein said means for sensing said intra-uterine pressure of said mother comprises a solid state pressure transducer.

26. A uterine monitoring system for measuring characteristics indicative of labor, said monitoring system comprising:

a remote sensing unit, said remote sensing unit containing means for sensing the intra-uterine pressure of a mother and for sensing electrical activity of a uterine muscle of said mother's uterus, said remote sensing unit also housing a first transceiver for outputting pressure and electromyogram signals;

an antenna for receiving said pressure and electromyogram signals from said first transceiver;

a monitoring station for monitoring said pressure and electromyogram signals, said monitoring station comprising a second transceiver for receiving said electromyogram and pressure signals from said antenna, a computing means for manipulating said electromyogram and pressure signals, and an output means for displaying information from said electromyogram and pressure signals, and means for sensing uterine temperature and for outputting a uterine temperature signal.

27. The uterine monitor recited in claim 26, wherein said computing means comprises a central processor, memory, arithmetic logic unit, and a communications bus for passing said electromyogram and pressure signals from said receiver to said output means.

28. The uterine monitor recited in claim 26, wherein said output means comprises a liquid crystal display.

29. The uterine monitor recited in claim 26, wherein said output means comprises a cathode ray tube.

30. The uterine monitor recited in claim 26, wherein said output means comprises a strip chart recorder.

31. The uterine monitor recited in claim 26, further comprising an automatic dispensing means for dispensing medication to said mother upon the existence of labor.

32. The uterine monitor recited in claim 31, wherein said automatic dispensing means comprises:

communications means for communicating with said determining means;

a pump for dispensing said medication;

a reservoir for maintaining said medication for said pump; and actuation means for receiving a signal from said communications means and for actuating said pump based upon said signal.

33. The uterine monitor recited in claim 32, wherein said communications means comprises a third transceiver.

34. The uterine monitor recited in claim 33, wherein said transceiver is a radio-telemetry transceiver.

35. The uterine monitor recited in claim 33, wherein each of said transceivers has a distinct predetermined frequency associated therewith, said predetermined frequencies for preventing accidental communication between said first, second and third transceivers 36. A uterine monitor for detecting onset of labor, said monitor comprising:

intra-uterine pressure sensing means implantable in a mother for providing a pressure signal representative of sensed intra-uterine pressure;

temperature sensing means implantable in said mother for providing a temperature signal representative of sensed uterine temperature; and signal processing means for receiving said pressure signal and said temperature signal, said signal processing means providing an output indicative of the onset of labor as a function of said pressure signal and said temperature signal.

37. The uterine monitor recited in claim 36, further comprising:

electromyogram sensing means implantable in said mother for providing an electromyogram signal representative of sensed uterine wall activity; and wherein said signal processing means provides said output indicative of the onset of labor as a function of said electromyogram signal and said pressure signal.

38. The uterine monitor recited in claim 37, wherein said signal processing means provides said output indicative of the onset of labor as a function of said temperature signal, said electromyogram signal, and said pressure signal.

39. A uterine monitor for detecting onset of labor, said monitor comprising:

electromyogram sensing means implantable in a mother for providing signal representative sensed uterine wall activity;

temperature sensing means implantable in said mother for providing a temperature signal representative of sensed uterine temperature; and signal processing means for receiving said electromyogram signal and said temperature signal, said signal processing means for providing an output indicative of the onset of labor as a function of said electromyogram signal and said temperature signal.

* * * * *